(12) United States Patent
van der Zel

(10) Patent No.: US 6,706,654 B2
(45) Date of Patent: Mar. 16, 2004

(54) PRESSABLE GLASS CERAMIC, METHOD FOR THE FABRICATION THEREOF, AND METHOD FOR THE FABRICATION OF A DENTAL RESTORATION USING SUCH GLASS CERAMIC

(75) Inventor: Joseph Maria van der Zel, Hoorn (NL)

(73) Assignee: Elephant Dental B.V., Hoorn (NL)

( * ) Notice: Subject to any disclaimer, the term of this patent is extended or adjusted under 35 U.S.C. 154(b) by 0 days.

(21) Appl. No.: 10/125,584

(22) Filed: Apr. 19, 2002

(65) Prior Publication Data

US 2002/0198093 A1 Dec. 26, 2002

(30) Foreign Application Priority Data

Apr. 20, 2001 (NL) .............................................. 1017895

(51) Int. Cl.⁷ ........................... C03C 14/00; C03C 8/02; A61C 13/08; C09K 3/00
(52) U.S. Cl. ............................. 501/32; 501/21; 501/17; 106/35; 264/16; 433/201.1; 433/202.1; 427/2.26; 427/2.27
(58) Field of Search .............................. 501/5–7, 14–18, 501/21, 27, 32; 106/35; 264/16; 433/201.1, 202.1; 427/2.26, 2.27

(56) References Cited

U.S. PATENT DOCUMENTS

| | | |
|---|---|---|
| 3,052,982 A | 9/1962 | Weinstein et al. |
| 4,101,330 A | 7/1978 | Burk et al. |
| 5,622,551 A | 4/1997 | Erbe et al. |
| 6,120,591 A | 9/2000 | Brodkin et al. |
| 6,342,458 B1 * | 1/2002 | Schweiger et al. ............ 501/5 |

FOREIGN PATENT DOCUMENTS

| | | |
|---|---|---|
| CA | 2213390 | 3/1998 |
| EP | 0475528 | 3/1992 |
| EP | 0536572 | 4/1993 |
| EP | 0827941 | 3/1998 |
| EP | 0916625 | 5/1999 |

OTHER PUBLICATIONS van der Zel, Jef M. et al, "The CICERO system for CAD/CAM fabrication of full–ceramic crowns", The Journal of Prosthetic Dentistry, vol. 85, No. 3, pp. 261–267 (Mar. 2001).

* cited by examiner

Primary Examiner—David R Sample
Assistant Examiner—Elizabeth Bolden
(74) Attorney, Agent, or Firm—Stevens, Davis, Miller & Mosher, LLP

(57) ABSTRACT

A pressable glass ceramic which contains lithium silicate glass and leucite is disclosed. Also, disclosed is the combination of leucite and a lithium silicate glass to stably increase the coefficients of thermal expansion of the resulting glass composition, and the preparation of leucite suitable for addition to the glass composition. Also disclosed are methods for fabricating glass ceramic and dental products from the pressable glass ceramic.

17 Claims, 2 Drawing Sheets

PRESSABLE GLASS CERAMIC, METHOD FOR THE FABRICATION THEREOF, AND METHOD FOR THE FABRICATION OF A DENTAL RESTORATION USING SUCH GLASS CERAMIC

FIELD OF THE INVENTION

The invention relates to a pressable glass ceramic, and in particular to a low-melting, high-expansion glass ceramic. Further, the invention relates to a method for the fabrication of such glass ceramic, and a method for the fabrication of a dental restoration using such glass ceramic. Finally, the invention relates to a component which makes it possible to increase the coefficients of thermal expansion (CTEs) of glass compositions, specifically in such a manner that the glass compositions, also after some temperature treatments, maintain a stable CTE.

In more detail, the invention relates to porcelains or ceramics of lithium disilicate glass which are plastically deformable under the influence of heat and pressure.

With the glass ceramic according to the invention, for instance all-ceramic dental restorations, inlays and onlays can be fabricated, but it can also be applied for carrying out repair on existing restorations or other types of dental prostheses and in combination with metal alloys.

BACKGROUND OF THE INVENTION

EP-A-0 827 941 discloses a sinterable lithium disilicate glass ceramic which has a CTE of 9–10 $\mu$m/m.K (measured in the temperature range of 20–500° C.). This is too low to allow firing on with conventional porcelain masses which are used for noble metal alloys. Since dental technicians most preferably work with porcelains that can be processed in an approximately equal manner and which possess substantially equal, at least compatible properties, it would be desirable to increase this relatively low CTE, in any case to above 12 $\mu$m/m.K (measured in the range of 20–500° C.).

More particularly, the press ceramic constituting the invention of EP-A-0 827 941, while having a high strength of fracture, a low pressing temperature and a reasonable translucency, has the disadvantage that the expansion is too low to allow firing on with current fire-on ceramics which for the greater part possess a higher coefficient of thermal expansion.

One of the options immediately eligible for this purpose is the addition of a leucite-containing high-expansion glass frit, since leucite, as is well known, raises the CTE. However, when known leucite-containing high-expansion glass frits, for instance Component 1 as described by Weinstein in his trend-setting U.S. patent U.S. Pat. No. 3,052,982 or high-expansion frits as described in EP-A-0 475 528, are added to the just described lithium disilicate glass according to EP-A-0 827 941, the proportion of aluminum oxide present in this high-expansion glass frit reacts with lithium silicate to form aluminum-lithium silicate, which exhibits a CTE around zero. Accordingly, instead of a CTE-increasing effect, the application of such known leucite-containing high-expansion frits has a lowering effect on the CTE value, so that the objective is not achieved. Further, investigations of the present inventor have shown that if after addition of high-expansion leucite-containing glass the lithium silicate material initially exhibits an increased expansion, further reactions between the leucite glass frit and the lithium silicate cannot be prevented when that material undergoes conventional processing heat treatments. This leads to the situation where during the different fire-on phases of the porcelain, a progressively decreasing CTE is found.

U.S. Pat. No. 6,120,591 discloses a dental porcelain which consists of a glassy matrix with crystals of tetragonal leucite embedded therein. This porcelain has a maturing temperature of 600–885° C. and a CTE of 11–19 $\mu$m/m.K (measured in the temperature range of from 25 to 500° C.). The tetragonal leucite is preferably fine-grained, and preferably has a diameter of 1–3 $\mu$m.

This tetragonal leucite is formed by mixing powdered metal oxides and metal carbonates in the appropriate proportions, whereafter the mixed powders are heated until a glass melt forms. This melt is quenched, whereafter the glass is heated to an elevated temperature of 950–1100° C. and thus held for 1–6 hours, whereby crystalline material is formed and grows further. Optionally, the quench step can be omitted.

DETAILED DESCRIPTION OF THE PREFERRED EMBODIMENTS

Figure 1:
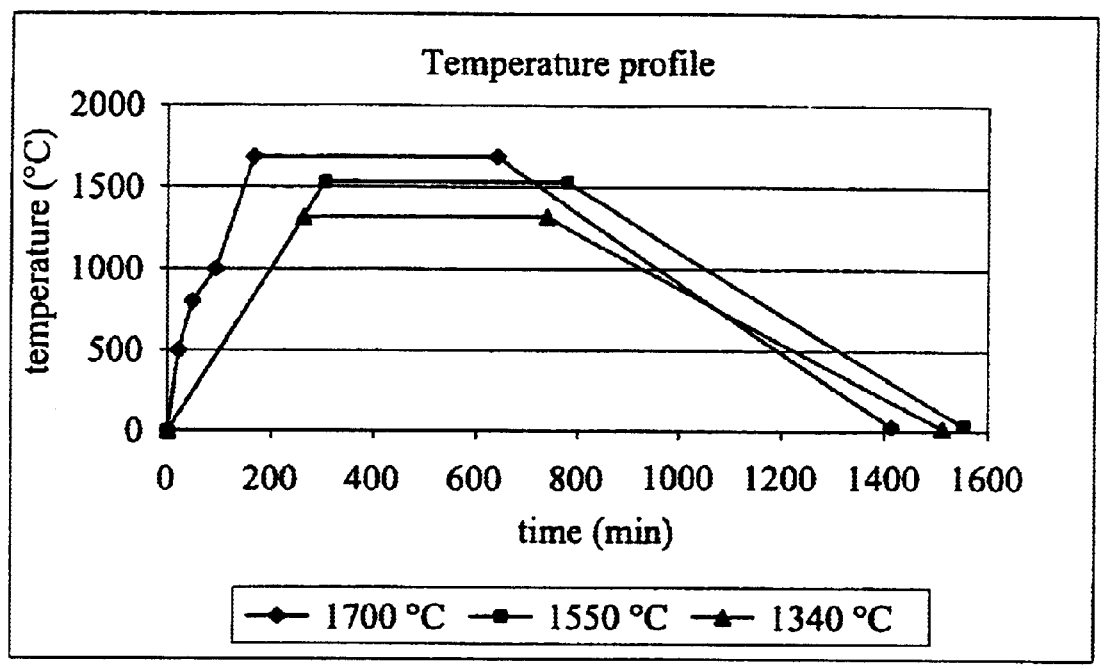
FIG. 1 shows the heat treatment profiles of the composite material.

The present inventor, in studying this system, has found that in the formation of leucite at 950–1100° C. from a molten glass phase, interactions occur between the leucite and the glass matrix: either leucite dissolves or leucite crystallizes further through interaction with the glass matrix. As a consequence of all this, in heat treatments the ceramic or porcelain product is not stable in the thermal expansion it exhibits, because the thermal expansion is directly related to the leucite content. Unless specified otherwise, in this description and in the claims the CTE has been determined in the temperature range of 20–500° C.

The present inventor has now found that by adding synthetic pure leucite in crystalline form to lithium silicate glass, it is possible to produce glass ceramics for the pressing of structures that possess a high and stable thermal expansion and a low pressing temperature, and which, as a consequence, can be fired on with the same ceramic masses as the conventional structures of fire-on alloys conventional in dentistry, having a coefficient of thermal expansion of 12–16 $\mu$m/m.K (measured in the temperature range of 20–500° C.). More particularly, it has surprisingly been found that if leucite is not added in the form of a high leucite glass frit but as a fine-ground pure synthetic leucite in crystalline form, this dissolving reaction does not occur. Through the amount of leucite added, the thermal expansion can be completely adjusted to the porcelain to be fired on, while during the different firing phases the thermal expansion does not decrease, as is the case upon conventional addition of high leucite frit.

Lithium silicate glass wets the synthetic pure leucite very well and imparts a high strength to the material. Thus, the invention makes it possible to provide a pressable, low-melting glass ceramic having sufficient strength and a high thermal expansion that is stable also after carrying out heating steps required in the processing.

Thus, the invention concerns in a first aspect a pressable glass ceramic, containing:

| lithium silicate glass | 30.0–90.0 wt. %; and |
| synthetic pure leucite | 10.0–70.0 wt. %. |

Another advantage is that with the addition of the inert leucite crystal the reactivity with the molding mass during pressing is reduced directly proportionally to the leucite-lithium silicate ratio.

Leucite ($K_2O.Al_2O_3.4SiO_2$) has a high coefficient of thermal expansion. Leucite can occur in two crystalline forms, viz. in tetragonal and cubic form. The reversible transition between tetragonal and cubic leucite occurs at 625° C., below 625° C. the tetragonal form is stable, above it, the cubic form. To increase thermal expansion, crystallization of tetragonal leucite is desirable; in fact, this crystalline form has an expansion of about 22 $\mu$m/m.K. Cubic leucite, by contrast, only has an expansion of about 10 $\mu$m/m.K Crystalline leucite can be prepared not only from feldspar, but also from mixtures of, for instance, $KHCO_3$, $Al_2O_3$ and $SiO_2$. These mixtures are composed so as to have the stoichiometric composition of leucite. Thus, after crystallization, theoretically up to 100 v/v % of leucite in the tetragonal phase can be formed. During the preparation method, it is to be ensured that no glass phase arises. Therefore the leucite is formed at temperatures below the melting point of the synthetic leucite, which is about 1650° C. In order to generate a sufficient conversion rate, the leucite is preferably synthesized above 1400° C. Very good results are obtained when the leucite is prepared from the powdered stag materials at a temperature between 1500 and 1630° C. Thus prepared leucite is called synthetic (pure) leucite. According to the present invention, use is made of this synthetic leucite in crystalline form without glass phase to increase the expansion of glass, and in particular lithium disilicate glass.

By making use of synthetic leucite, the reaction with lithium disilicate is prevented. Synthetic leucite has a high melting point (about 1685° C.) and, surprisingly, does not react during the sintering (1000° C.); this in contrast to leucite which crystallizes from a glass phase, such as leucite recovered from feldspar.

It is incidentally noted that the preparation of synthetic leucite is known per se.

U.S. Pat. No. 4,101,330 describes a method for preparing synthetic leucite. This (synthetic) leucite is introduced into nepheline syenite and in this combination recommended as raw material for, for instance, dental applications for increasing the thermal expansion of the glass to which it is added.

The leucite/nepheline-syenite material described also contains sodium, potassium and lithium carbonates. Moreover, nepheline syenite contains much aluminum silicate. This gives rise to the same problem upon use with lithium silicate glass as that outlined hereinabove in connection with EP-A-0,827,941.

U.S. Pat. No. 5,622,551 also describes synthetic tetragonal leucite as a component in dental porcelain and points to the setting of coefficients of thermal expansion. The glass compositions in which it is incorporated are alkali metal aluminum-silicate glass compositions. The problems of lithium glass compositions and the solution according to the invention are again not given.

The synthetic leucite such as it is used according to the invention is preferably obtained from a method for preparing the synthetic leucite, wherein at least potassium carbonate, aluminum oxide and silicon oxide in the proportion desired for leucite, in powder form with preferably a particle size of less than 100 $\mu$m, are mixed, preferably by grinding, the mixture is heated in an oven to a temperature between 1400° C. and the melting temperature of the leucite to be formed. The heating step typically takes about 1 to 10 hours. The sintered, thus obtained leucite is subsequently reduced to a powder having an average grain size of from 1 to 100 $\mu$m.

In a second aspect, the invention is directed to the use of synthetic leucite for stably increasing the thermal expansion of a glass composition. Here, stable is understood to mean that the thermal expansion upon five-time subjection to a heating step, when measured after each heating step, has a CTE value deviating form the average by less than 0.4 $\mu$m/m.K.

In the fist aspect, the invention, as stated, is directed in particular to lithium disilicate glass ceramic modified with synthetic pure leucite. In the lithium silicate glass, $Li_2O$ and $SiO_2$ are present in a mutual weight ratio of between ¼ and ⅔₈.

The glass ceramic is produced by melting the raw materials and quenchiug the melt, so that glass granulate is formed. The glass is dried and ground. The composition of the lithium disilicate has a low viscosity at 700–900° C. and is consequently highly suitable as a press ceramic. The CTE (±10 $\mu$m/m.K) of the glass ceramic, however, is too low to fire on with ceramic masses conventional for metal ceramic.

Highly suitable lithium disilicate glass compositions to which the synthetic pure leucite according to the invention can be added are described in European patent application EP-A-0 536 572. The lithium silicate glass compositions described and prepared in and according to this EP-A are incorporated into the present description by reference. More in detail, the lithium disilicate glass compositions described there are prepared from 8–19% $Li_2O$; 0–5%$Na_2O$; 0–7% $K_2O$; 0–8% $Na_2O+K_2O$; 0–10% CaO; 0–6% SrO; 0–6% BaO; 2–12% ($Na_2O+K_2O+CaO+SrO+BaO$); 0–7% ZnO; 0–11% $Al_2O_3$; 1.5–11% $ZnO+Al_2O_3$; wherein the molar ratio between ($Na_2O+K_2O+CaO+SrO+BaO$) and ($ZnO+Al_2O_3$) is between 0.075 and 1.25; and wherein the balance consists of $SiO_2$, wherein as nucleation agent 1.5–7% $P_2O_5$ and/or 0.0001–0.1% Pd is present, while optionally colorants or other conventional processing aids and additives can be present. Here, all percentages are percentages by weight based on the weight of the total composition, just as in the rest of this description, unless specified otherwise.

Also in EP-A-0 916 625, the preparation of dental products consisting of lithium disilicate glass ceramics is described. The lithium disilicate compositions described there can be applied in the present invention, and these compositions are incorporated into the present description by reference.

Also suitable are the compositions such as they are described in the EP-A-0 827 941 already mentioned. In these compositions, which are likewise incorporated into this description by reference, it is required, according to the invention in said EP-A, that 0.1–6% $La_2O_3$ be present, which component is redundant for the present invention, at any rate merely an optional ingredient. The compositions from this reference contain: 57–80% $SiO_2$; 11–19% $Li_2O$; 0–5% $Al_2O_3$; 0.1–6% $La_2O_3$; wherein the content of $Al_2O_3+La_2O_3$ is 0.1–7%; 0–5% MgO; 0–8% ZnO; wherein the content of MgO+ZnO is 0.1–9%; 0–11% $P_2O_5$; and 0–13.5% $K_2O$; while moreover colorants and additives are present.

The synthetic leucite is used in an amount between 10 and 70 wt. %. At a percentage by weight of leucite higher than 70%, the individual leucite particles touch each other and the lithium silicate functions only as infiltrate between the granules. In fact, the best results in terms of strength and stability are obtained when the upper limit for leucite is at 60% and preferably at 50 wt. %. The lower limit of 10% is less critical; and is in fact determined by the CTE value contemplated for the total composition. Typically, between 20 and 50 wt. % synthetic leucite will be used.

In addition to the essential ingredients of the pressable ceramic according to the invention, conventional color components can be present in amounts of 0–8.0 wt. %; as well as other additions known per se for press ceramics for dental applications in amounts of, for instance, 0–6.0 wt. %. Preferably, the color components consist of glass coloring oxides (a) and/or of solid color particles (b) such as they are described in the above-mentioned EP-A-0 827 941 in the amounts also specified there. Preferably, as glass coloring oxides $TiO_2$, $CeO_2$ and/or $Fe_2O_3$ are used, whilst as solid color particles spinel can be present. Examples of other additions are $ZrO_2$ and $Al_2O_3$.

Further, the invention relates to a method for the fabrication of such a glass ceramic, wherein 30–90 parts by weight of a powdered lithium silicate glass and 10–70 parts by weight of powdered synthetic leucite are mixed and the mixture is heated under vacuum until a sintered-up product is obtained.

For instance, synthetic leucite having an average grain size between 1 and 100 $\mu$m, preferably between 1 and 40 $\mu$m, more preferably between 1 and 10 $\mu$m and most preferably between 1 and 5 $\mu$m is intensively mixed with glass ceramic powder. The coarser the leucite, the less strong will be the glass ceramic to be eventually obtained. Moreover, in the use of smaller leucite granules fewer stresses arise in the eventual glass. When using the leucite particles in the range of 1–5, and preferably 1–3 $\mu$m, the ceramic or porcelain can in fact be fired ad infinitum without cracking occurring.

This glass ceramic powder can be obtained, for instance, by melting a suitable lithium silicate glass—incidentally, without any solid color particles to be optionally used—for instance at a temperature between 1100 and 1700° C., subsequently pouring this melt into water, thereby forming a granulate, and then grinding this glass granulate to the desired grain size. The degree of grinding of the glass granulate is at an average grain size between 1 and 100 $\mu$m, preferably between 1 and 40 $\mu$m, and preferably between 1 and 10 $\mu$m; preferably, this degree of grinding corresponds to the degree of grinding of the leucite. Mixing is done is a weight ratio of 70/30 to 10/90 (leucite/lithium silicate glass), whilst intensive mixing can be done by grinding or in any other manner. To the powder mixture thus to be prepared, the solid color particles and other desired additives can be added as well. Then the powder is suitably pressed to form a pellet of predetermined dimensions. The glass ceramic pellet is subsequently subjected, under vacuum and at a temperature of typically 400 to 1100° C., though in any case at a temperature at which the leucite particles do not melt, to one or more heat treatments to effect sintering up. The thus obtained compacted pellet is to be used as dental raw material.

To that end, the invention also relates to a method for fabricating a dental product, wherein the sintered-up product obtained, by mixing 30–90 parts by weight of a powdered lithium silicate glass and 10–70 parts by weight of powdered synthetic leucite and then heating the mixture under vacuum until the sintered-up product is obtained, is pressed at an elevated temperature, though at a temperature lower than the melting point of the synthetic leucite, and preferably at a temperature of 700–1200° C., and through application of pressure, preferably a pressure of 2–10 bars, to form a dental restoration. Such pressing is preferably machined.

The dental restoration can subsequently be fired on with a fire-on porcelain, or, as a coating, a ceramic, a sintering ceramic, a glass ceramic, a glass, a glaze, and/or a composite can be applied. The coating suitably has a sintering temperature of 650–950° C. and a linear thermal expansion coefficient which is lower than that of the dental product to be coated. Preferably, the linear thermal expansion coefficient of the coating does not deviate by more than +/−3.0 $\mu$m/m.K from that of the dental product.

The leucite-modified lithium silicate glass ceramic according to the invention satisfies the expansion requirements of conventional porcelain fire-on masses. The pressability of the material is good. To be able to press and fire on the material with, for instance, Carrara® porcelain, it must satisfy the following requirements.

The pressing temperature must be below 1130° C., so that it is suitable for use in the ovens of a dental laboratory. To reduce the reactivity of the material with the embedding mass, the actual pressing temperature will have to be below 1000° C.

The Coefficient of Thermal Expansion (C.T.E.) is preferably in the range of $15.0 \pm 0.3 * 10^{-6}$° $C.^{-1}$ (measured in the range of 25–500° C). The material must be thermally and dimensionally stable during five times firing at temperatures above 850° C.

Further, the invention relates to a method for fabricating a dental product, comprising fabricating a dental restoration or a support structure for porcelain to be fired on, by milling a sintered-up product obtained from the above-described method for fabricating a glass ceramic, and optionally firing on porcelain. Further, the invention relates to a method for fabricating a dental products comprising partially sintering a glass ceramic according to the invention, followed by fabricating therefrom a dental restoration or a support structure for porcelain to be fired on, by grinding the partially sintered glass ceramic in a form enlarged by the sintering shrinkage factor; and subsequently sintering the ground product to the end density. In this embodiment, the glass ceramic is not sintered up completely in a first step. The sintering process is interrupted at a suitable moment, viz. when embossing arises between the particles to be sintered. This takes place, for instance, and preferably so, by presintering for a few minutes (3–10 minutes, preferably 5 minutes) at a temperature of some 750–850° C. The final sintering can take place, for instance, and preferably so, by sintering for a few minutes (3–10 minutes, preferably 5 minutes) at a temperature of about 900–1050° C.

When presintering is done, the density is less, and hence the volume of the presintered product is greater than that of the restoration or support structure contemplated. The dental technician will take account of this by using a form tailored to the sintering shrinkage factor.

In both methods just described, grinding is preferably carried out utilizing a computer-controlled milling machine, controlled by a data file generated by a computer-assisted design system. Such CAD-CAM systems are known and are described inter alia in the "The CICERO system for CAD/CAM fabrication of full ceramic crowns" by Jef M. van der Zel et al. in The Journal of Prosthetic Dentistry, Vol. 85, no. 3 (March 2001), pp. 261–267.

The method for fabricating a dental product will presently be discussed in more detail, though without the embodiment discussed being intended to limit the method.

Before a patient is fitted with, for instance, a crown, the natural tooth must be milled back to a stub. Of the stub, a gypsum model is made. Onto the gypsum model, a wax layer is applied of about 0.7 mm in thickness. Onto the top of the cap, a runner channel is provided having a diameter of 2–3 mm and a length of 5–6 mm. After modelling the cap, it is properly blown dry and taken from the gypsum model. For tests in a laboratory, a metal model can be used, because it is reusable.

The wax cap is attached to a muffle base. The cylinder to which the cap is attached eventually forms the press channel. Onto the muffle base a paper cylinder is fixed having thereon a plastic ring for strengthening. The whole is then filled with a conventional embedding mass; during filling, the muffle base stands on a vibration plate to remove air bubbles from the embedding mass. After filing, the embedding mass is hardened by allowing it to stand at room temperature for a particular time. After hardening, the paper cylinder and the muffle base can be removed. What is left is a cylinder of hardened embedding mass (the muffle).

The wax cap that is still in the muffle is evaporated at high temperature. What is presently left in the muffle is a cavity having the shape of the wax cap.

The muffle is now ready for the pressing procedure. To that end, the muffle is taken hot from the burnout oven and subsequently a press pellet of the ceramic according to the invention is laid in the press channel. Subsequently a cylinder of aluminum oxide (plunger) is slipped into the press channel; the cylinder is an exact fit with respect to the press channel. Subsequently, the whole is placed in a Cera Quick Press® oven. The oven traverses a heat treatment to bring the muffle to the correct pressing temperature. The muffle is subsequently taken from the oven and laid under the press, which presses the cylinder into the muffle under the pressure set and maintains this pressure for a particular time.

The pressing parameters such as temperature and pressure are of importance in pressing. The temperature must be high enough to make the material sufficiently viscous to press it, but not so high as to cause the material to react with the embedding mass. The pressure and the duration of the pressure must be controlled such that a minimal porosity remains behind in the cap.

After the muffle has been cooled off, the cap can be unbedded. The penetration depth of the plunger is marked and this portion is removed with the aid of a diamond saw. The embedding mass is subsequently removed by sand blasting it with glass beads of 50 $\mu$m at a pressure of 2–2.5 bar.

After unbedding, a cap is left which is attached to the plunger by way of the runner channel. This runner channel is removed.

Onto the cap, subsequently, porcelain can be fired to thereby form a crown. After each firing-on cycle, the fit can be checked by fitting the cap onto the metal model. The cap must not have deformed after five firing cycles.

EXAMPLES

The invention will presently be further described with reference to the following, non-limiting examples.

In the examples, a feldspathic lithium silicate glass frit has been made, consisting of 13 mass % feldspar, 33 mass % lithium oxide and 54 mass % silicon oxide. In addition to this composition, a lithium silicate glass has been made, to which $P_2O_5$, has been added as nucleation agent. The weighed chemicals are mixed in a tilting mixer and then placed in the oven in mullite crucibles. The oven is heated with a gradient of 1.3° C./min to 1340° C. and then remains at this temperature for 4 hours. Upon heating, all chemicals decompose to the oxide form. To allow escape of the reaction products in the form of gas bubbles the viscosity of the melt must be low enough and hence the temperature high enough. To make sure that all chemicals have decomposed, the oven is held at 1340° C. for 4 hours.

After the oven cycle, the glass melt is poured out into water (quenching). As a result of the temperature shock (from 1340° C. to 25° C.), the glass falls apart as a granulate. The granulate is dried and ground to powder (glass frit; grain size <106 $\mu$m). The CTE $\alpha_{25-500°\ C.}=9.86*10^{-6°}\ C.^{-1}$ and the strength is ±200 MPa.

Example 1 (Comparison)

A high-leucite glass frit (Component 1 from U.S. Pat. No. 3,052,982) was mixed with the lithium silicate described, in a weight ratio of 40:60. The expansion values are given in Table 1. The coefficient of thermal expansion decreases progressively with each firing phase.

Example 2

For the production of synthetic leucite, three different methods were followed and compared with each other. The three methods started from the same composition of chemicals ($K_2CO_3$ 28.8 wt. %; $Al_2O_3$ 21.2 wt. %; $SiO_2$ (cristoballite) 50%) which after different heat treatments are converted to tetragonal leucite. Only the method that was carried out at 1550° C. yielded a good product; the method that was carried out at 1700° C. yielded a glass phase, which gives rise to instabilities; the method at 1340° C. gave an insufficient conversion to leucite.

Figure 2:
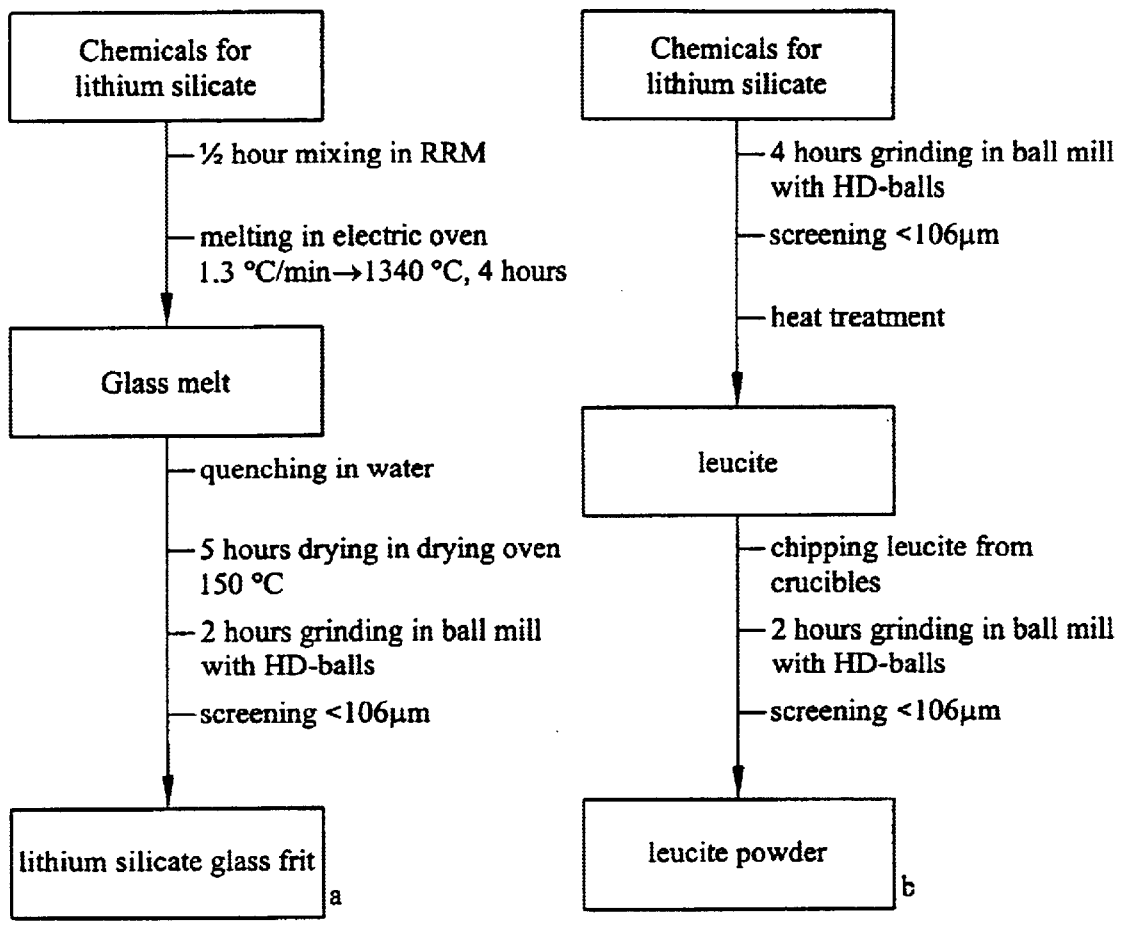
FIG. 2 shows a flow chart of the production of the leucite.

The most important difference in the heat treatment is the maximum temperature. These are 1700° C., 1550° C. and 1340° C., see FIG. 1. The leucite was produced according to the flow diagram in FIG. 2.

Of the sintered pellets, subsequently, bars were sawn and ground for the strength and expansion tests.

Preparing Leucite at 1550° C.

The leucite has not drawn into the crucibles, because there is no discoloration to be seen on the outside of the crucible. With the leucite prepared at 155° C. examples are made. The temperature cycle with 1550° C. as maximum temperature has an $\alpha_{25-500°\ C.}=14.30*10^{-6°}\ C.^{-1}$ and a strength of 131 MPa. These values are below the expansion requirement of $15.00\pm0,30*10^{-6°}\ C.^{-1}$ and strength target value of ±200 MPa, but can sill be optimized.

The product obtained at 1550° C. was tested according to Example 1.

The results are shown in Table 1.

TABLE 1

| Firing cycle | $\alpha_{25-500°\ C.}$ ($*10^{-6°}\ C.^{-1}$) | | Firing cycle | $\alpha_{25-500°\ C.}$ ($*10^{-6°}\ C.^{-1}$) | |
|---|---|---|---|---|---|
| | Example 1 | Example 2 | | Example 1 | Example 2 |
| 0[1] | | | | | |
| 1 | 14.95 | 14.30 | 5 | — | 14.88 |
| 2 | 13.43 | 14.80 | 6 | — | 14.71 |
| 3 | 12.80 | 14.60 | 7 | — | 14.63 |

TABLE 1-continued

| Firing cycle | $\alpha_{25-500° C.}$ ($*10^{-6} \, °C.^{-1}$) | | Firing cycle | $\alpha_{25-500° C.}$ ($*10^{-6} \, °C.^{-1}$) | |
| --- | --- | --- | --- | --- | --- |
| $0^1$ | Example 1 | Example 2 | cycle | Example 1 | Example 2 |
| 4 | 11.50 | 14.83 | 8 | — | 14.89 |
|  | — | 14.96 |  |  |  |

[1]Measured after sintering, without firing-on cycle

What is claimed is:

1. A pressable composite material comprising a glass and a ceramic, containing a mixture of:

| | |
| --- | --- |
| lithium silicate glass | 30.0–90.0 wt. %; and |
| synthetic pure leucite in crystalline form | 10.0–70.0 wt. %. |

2. The composite material according to claim 1, wherein in the lithium silicate glass $Li_2O$ and $SiO_2$ are present in a mutual weight ratio of $Li_2O$ to $Si_2O$ between ¼ and ⅔.

3. The composite material according to claim 1, wherein the lithium silicate glass further contains 0–8.0 wt. % total of one or more additives selected from the group consisting of $Al_2O_3$, $La_2O_3$, MgO, ZnO, $K_2O$, $P_2O_5$, $B_2O_3$, F, $Na_2O$, $ZrO_2$, BaO and SrO.

4. A method for fabricating a composite material according to claim 1, wherein 30–90 parts by weight of a powdered lithium silicate glass and 10–70 parts by weight of powdered synthetic leucite in crystalline form are mixed and the mixture is heated under vacuum until a sintered-up product is obtained.

5. A method for fabricating a dental product, wherein the sintered-up product obtained according to claim 4 is pressed at an elevated temperature, though at a temperature lower than the melting point of the synthetic leucite, and through the application of pressure, to form a dental restoration.

6. A method according to claim 5, wherein the dental restoration is fired on with a fire-on porcelain, or, as a coating, a ceramic, a sintering ceramic, a glass ceramic, a glass, a glaze, and/or a composite is applied.

7. A method for fabricating a dental product, comprising fabricating a dental restoration or a support structure by milling a sintered-up product obtained from the method according to claim 4 and optionally firing it on with porcelain.

8. A method for fabricating a dental product, comprising partially sintering a composite material according to claim 1; fabricating a dental restoration or a support structure therefrom by grinding that partially sintered composite material into a form enlarged by the sintering shrinkage factor; and sintering the ground product to final density.

9. A method according to claim 7, wherein the milling is carried out utilizing a computer-controlled milling machine, controlled by a data file generated by a computer-assisted design system.

10. The composite material according to claim 2, wherein the lithium silicate glass further contains 0–8.0 wt. % of $Al_2O_3$, $La_2O_3$, MgO, ZnO, $K_2O$, $P_2O_5$, $B_2O_3$, F, $Na_2O$, $ZrO_2$, BaO and/or SrO.

11. A method for fabricating a dental product, comprising partially sintering a composite material according to claim 2; fabricating a dental restoration or a support structure therefrom by grinding that partially sintered composite material into a form enlarged by the sintering shrinkage factor; and sintering the ground product to final density.

12. A method according to claim 8, wherein the grinding is carried out utilizing a computer-controlled milling machine, controlled by a data file generated by a computer-assisted design system.

13. A method according to claim 5, wherein the sintered-up product is pressed at a temperature of 700–1200° C., and through the application of a pressure of 2–10 bars, to form the dental restoration.

14. The composite material according to claim 1, wherein the synthetic leucite has a melting point of about 1685° C.

15. The composite material according to claim 1, wherein the synthetic leucite is a powder.

16. The composite material according to claim 1, wherein the synthetic leucite has an average grain size of from 1 to 100 μm.

17. The composite material according to claim 1, wherein the composite material comprises 20–50 wt. % said synthetic pure leucite.

* * * * *